(12) United States Patent
Chen et al.

(10) Patent No.: US 10,548,479 B2
(45) Date of Patent: *Feb. 4, 2020

(54) OPTICAL COHERENCE ELASTOGRAPHY (OCE) METHOD UNDER ACOUSTIC RADIATION FORCE EXCITATION USING OCT DOPPLER VARIANCE METHODS AND OCT CORRELATION-BASED METHODS

(71) Applicant: The Regents of the University of California, Oakland, CA (US)

(72) Inventors: Zhongping Chen, Irivne, CA (US); Jiang Zhu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 945 days.

This patent is subject to a terminal disclaimer.

(21) Appl. No.: 15/043,539

(22) Filed: Feb. 13, 2016

(65) Prior Publication Data
US 2016/0242650 A1 Aug. 25, 2016

Related U.S. Application Data

(60) Provisional application No. 62/116,854, filed on Feb. 16, 2015.

(51) Int. Cl.
*A61B 5/00* (2006.01)
*A61B 3/10* (2006.01)
*G06T 7/00* (2017.01)

(52) U.S. Cl.
CPC ............ *A61B 5/0066* (2013.01); *A61B 3/102* (2013.01); *G06T 7/0012* (2013.01); *A61B 5/0084* (2013.01)

(58) Field of Classification Search
CPC ... A61B 5/0066; A61B 5/0035; A61B 5/0051; A61B 5/0071; A61B 8/4416; A61B 8/485; A61B 8/00; A61B 8/08
See application file for complete search history.

(56) References Cited

U.S. PATENT DOCUMENTS

2015/0351722 A1* 12/2015 Chen ...................... A61B 8/485
600/427

* cited by examiner

*Primary Examiner* — Carolyn A Pehlke
(74) *Attorney, Agent, or Firm* — Marcus C. Dawes; Daniel L. Dawes

(57) ABSTRACT

A system for imaging and quantifying shear wave and shear modulus under orthogonal acoustic radiation force (ARF) excitation using the OCT Doppler variance apparatus. The ARF perpendicular or with at least a perpendicular component to the OCT beam is produced by a remote ultrasonic transducer. The OCT Doppler variance apparatus, which is sensitive to the transverse vibration, is used to measure the ARF induced vibration. For analysis of the shear modulus, the Doppler variance apparatus is utilized to visualize shear wave propagation. The propagation velocity of the shear wave is measured and then used to quantitatively map the shear modulus.

17 Claims, 11 Drawing Sheets
(5 of 11 Drawing Sheet(s) Filed in Color)

OPTICAL COHERENCE ELASTOGRAPHY (OCE) METHOD UNDER ACOUSTIC RADIATION FORCE EXCITATION USING OCT DOPPLER VARIANCE METHODS AND OCT CORRELATION-BASED METHODS

GOVERNMENT SUPPORT

This invention was made with government support under Grant Nos. 021529 and 125084, funded by the National Institutes of Health. The government has certain rights in the invention.

RELATED APPLICATIONS

This application is related to provisional patent application, entitled Optical Coherence Elastography (OCE) Method Under Acoustic Radiation Force Excitation Using OCT Doppler Variance Methods and OCT Correlation-Based Methods, Ser. No. 62/116,854, filed on Feb. 16, 2015, under 35 USC 119, which is incorporated herein by reference.

BACKGROUND

Field of the Technology

The invention relates to the field of optical coherence elastography (OCE), specifically an OCE method under acoustic radiation force excitation using OCT Doppler variance and OCT correlation based techniques.

Description of the Prior Art

The process of elastography is able to noninvasively image and measure the elastic properties of a soft tissue and has been used for medical diagnosis and tissue characterization. In the last decade, optical coherence tomography (OCT) has revealed the superiority of elastography due to its high speed and high spatial resolution imaging. In an optical coherence elastography (OCE) application, the OCT unit is used for detection of elastic vibration, and different mechanical excitation sources are employed to generate an elastic wave in the soft materials, including a focused air-puff device, an acoustic radiation force, a mechanical wave driver and a piezoelectric actuator. Since an acoustic radiation force (ARF) can generate elastic vibration inside the tissue without contact, it may be preferable for clinical diagnosis. ARF based OCE (ARF-OCE) has been employed to measure the shear wave and the longitudinal vibration. In previous shear wave detection using ARF-OCE methods, phase changes were detected by a Doppler OCT unit. The transducer and the OCT unit were located either on the same or opposing sides of the detected sample, and ARF induced axial displacement is parallel to the OCT detection beam.

However, there are many clinical cases, such as cornea imaging, where ARF excitation direction perpendicular or with at least a perpendicular component to the OCT beam is more convenient to implement. In addition, the phase changes may be distorted by bulk motion and phase wrapping, and high phase stability and subsequent data correction are required for phase-resolved OCT. Moreover, shear wave attenuation is rather large so the detectable range along its propagation direction is very limited

BRIEF SUMMARY

In the illustrated embodiments of the invention the acoustic radiation direction is perpendicular or at least a perpendicular component to the optical detection direction and the ARF-induced tissue vibrations are detected by an Doppler variance method instead of Doppler OCT methods, including phase resolved Doppler variance and intensity based Doppler variance.

The current invention is a method for imaging the shear wave and quantifying shear modulus under orthogonal acoustic radiation force (ARF) excitation using an optical coherence tomography (OCT) Doppler variance method. ARF-induced vibration perpendicular or with at least a perpendicular component to the OCT beam is induced by a remote ultrasonic transducer and is detected by an OCT Doppler variance method. Shear modulus of a volume in a tissue is quantitatively mapped after employing the lateral and transverse scan. This method provides an imaging modality to map the elastic properties of a tissue.

What is disclosed is an ARF-OCE system where the acoustic radiation direction is perpendicular or has at least a perpendicular component to the optical detection direction and the ARF-induced tissue vibrations are detected by a Doppler variance method instead of Doppler OCT method. Either phase-resolved Doppler variance or intensity-based Doppler variance (IBDV) or both are used to measure the transverse vibration. Using this system, a direct measurement of the propagation velocity of the shear wave at different depths of one location with an M scan is made and then used to quantitatively map the shear modulus of a cross-section in a tissue-equivalent phantom after employing a cross-sectional B scan. Since Doppler variance is used, this system is less sensitive to bulk motion and also requires less data processing.

Thus, the illustrated embodiments of the invention include a method for imaging shear wave or quantifying shear modulus in tissue under orthogonal acoustic radiation force (ARF) excitation using an optical coherence tomography (OCT) Doppler variance comprising the steps of: generating an OCT beam in the tissue; generating ARF-induced vibration in the tissue with at least a perpendicular component to the OCT beam in the tissue by an ultrasonic transducer; and detecting ARF-induced vibration in the tissue using an OCT Doppler variance method or an OCT correlation-based method.

The method further comprises the steps of imaging a shear wave propagation parallel to the OCT beam with an M scan at each location and quantitatively measuring a slope of a propagation path to calculate shear modulus at the location.

The method further comprises the step of quantitatively mapping a shear modulus of a volume in the tissue by employing a lateral and transverse scan as an imaging modality to map an elastic property of the tissue.

The step of detecting ARF-induced vibration in the tissue using an OCT Doppler variance method or an OCT correlation-based method comprises the step of using phase resolved Doppler variance or intensity based Doppler variance (IBDV) quantitative measurement.

The method further comprises the step of quantitatively mapping the shear modulus of a cross-section in the tissue by employing a cross-sectional B scan.

The method further comprising the step of quantitatively mapping Young's modulus, velocity of shear wave or a combination thereof of a volume in the tissue by employing a lateral and transverse scan as an imaging modality.

The step of generating ARF-induced vibration in the tissue with at least a perpendicular component to the OCT beam in the tissue by an ultrasonic transducer comprises the step of generating the ARF-induced vibration by a remote ultrasonic transducer applying a non-contact force to the tissue, or generating the ARF-induced vibration by an ultrasonic transducer applying a contact force to the tissue.

The step of generating ARF-induced vibration in the tissue with at least a perpendicular component to the OCT beam in the tissue by an ultrasonic transducer comprises the step of generating an ARF-induced vibration which is perpendicular or has at least a perpendicular component to the OCT beam.

In one embodiment the steps of generating an OCT beam, generating ARF-induced vibration in the tissue and detecting ARF-induced vibration in the tissue comprises practicing these steps using an endoscope-based system or a bench system.

In another embodiment the steps of generating an OCT beam, generating ARF-induced vibration in the tissue and detecting ARF-induced vibration in the tissue comprises practicing these steps using a multimodality system incorporating OCT system.

The step of practicing these steps using a multimodality system incorporating OCT system comprises practicing these steps in an integrated ultrasound-OCT system, integrated photoacoustic-OCT system or integrated fluorescence.

The method is intended to be performed on cancer tissue, ocular tissue, periocular tissue or vascular tissue.

The method further comprises the steps of diagnosing the tissue, and treating the tissue when diagnosed with cancer, an ocular disease, or a cardiovascular disease.

The scope of the invention is such that it expressly includes an apparatus for imaging shear wave or quantifying shear modulus in tissue under orthogonal acoustic radiation force (ARF) excitation using an optical coherence tomography (OCT) Doppler variance comprising: an OCT subsystem for generating an OCT beam in the tissue; an ARF subsystem for generating an ARF-induced vibration in the tissue with at least a perpendicular component to the OCT beam in the tissue by an ultrasonic transducer; and a detector for detecting ARF-induced vibration in the tissue using an OCT Doppler variance apparatus or an OCT correlation-based apparatus.

The ARF subsystem comprises a remote ultrasonic transducer applying a non-contact force to the tissue or an ultrasonic transducer applying a contact force to the tissue.

The OCT and ARF subsystems are included within an endoscope-based system or a bench system.

The OCT and ARF subsystems are included within a multimodality system.

The multimodality system comprises an integrated ultrasound-OCT system, integrated photoacoustic-OCT system or integrated fluorescence-OCT system.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application the contains at least one drawing executed in color. Copies of this patent or patent application publication with color drawing(s) will be provided by the Office upon request and payment of the necessary fee.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
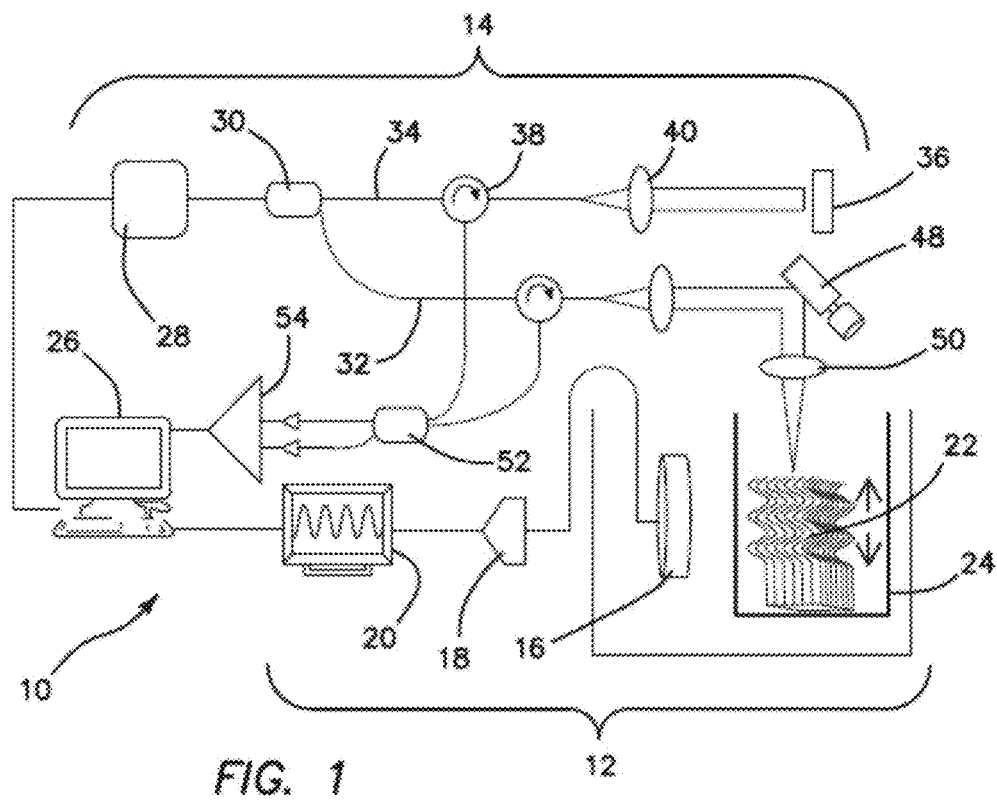
FIG. 1 is a diagram of an experimental setup for shear modulus measurement using ARFOE-OCE.

An experimental schematic of the ARF-OCE system 10 is illustrated in FIG. 1. The acoustic radiation direction is perpendicular or has at least a perpendicular component to the optical detection direction. ARF induced vibration is perpendicular or has at least a perpendicular component to the OCT beam and the shear wave propagates along the OCT beam. System 10 includes two subsystems: an ARF generation subsystem 12 and an OCT subsystem 14. A phantom 22 is disposed within a water tank 24. For ARF generation, an ultrasonic transducer 16 with a resonant frequency of 4.5 MHz, a focus length of 29.7 mm, an axial full width at half-maximum power (FWHM) of 8 mm and diameter of 20 mm is driven by a burst consisting of 4500 cycles of a sine wave generated by function generator 20 amplified by a broadband power amplifier 18, corresponding to a 1.0 ms emission at 160 V peak-to-peak. The transduced ultrasound echo is returned to a computer 26.

The OCT subsystem 14 is based on a swept source 28 with a central wavelength of 1310 nm, an A-line speed of 50 KHz, and a total average power of 16 mW. A 90/10 coupler 30 separates 90% of the laser light to the sample arm 32 and 10% to the reference arm 34. The light in reference arm 34 is transmitted through a circulator 38 to a collimator 40 and then reflected from a mirror 36 back to circulator 38 and thence to 50/50 coupler 52. Light in sample arm 32 is directed by fiber optics to circulator 42, collimator 46, and a two axial galvo mirror 48 for generating a scanning beam and through focusing lens 50 with a focusing length of 36 mm onto specimen or phantom 22. Light scattered from the specimen 22 is returned to and interferes in 50/50 coupler 52. The reference signal and the sample signals are measured by a dual-balanced detector 54. The output of detector 54 is then coupled to computer 26 for data processing. The axial resolution of the OCT image is 9.72 µm/pixel.

In order to measure the propagation velocity of the shear wave at one location, 1000 A-lines at a rate of 50 KHz are involved in one M scan. Each M scan totally takes 20.0 ms and contains a burst of 1.0 ms for ARF generation at the beginning of each M scan. For two dimensional mapping of the shear modulus, a galvo mirror scanning unit in the sample arm is controlled by a programmed trigger. For two dimensional mapping of the shear modulus, a B-scan contains 500 k A-lines at 500 lateral positions. After the alignment using a hydrophone, OCT beam scans along the ARF direction directly above the ARF focus area, so the wave propagation is simplified in a two dimensional plane. Considering the propagation direction and velocity, the detected wave along the OCT beam is dominated by the shear wave. The B-scan range is about 2.7 mm, which is much smaller than ARF FWHM, and so the induced wave is simplified to be a plane shear wave propagating parallel to the OCT beam in this range.

The tissue-equivalent phantom is placed in a thin-film container 24 through which the ultrasound can pass. The thin-film container 24 and US transducer 16 are immersed in water. The acoustic radiation direction is perpendicular or has at least a perpendicular component to the OCT detection direction.

In order to extract the vibration information from the OCT data, Doppler variance methods are employed, which are sensitive to the transverse vibration. As the IBDV method and phase-resolved Doppler variance method provide similar measurement results, only the IBDV method is illustrated here. Briefly, the vibration intensity is directly related to the intensity-based Doppler variance $\sigma^2$, which is calculated by the following equation:

$$\sigma^2 = 1 - \frac{\sum_{i=1}^{M}\sum_{z=1}^{N}(|I_{i,z}| \cdot |I_{i+1,z}|)}{\frac{1}{2}\sum_{i=1}^{M}\sum_{z=1}^{N}(|I_{i,z}|^2 + |I_{i+1,z}|^2)}, \quad (1)$$

where $I_{x,z}$ is the complex data at the A-line of i and the depth of z. Both M and N are equal to 4 for lateral and depth averaging in this embodiment. This method uses intensity information for vibration detection instead of phase information. It especially works better if the vibration direction is perpendicular to the optical detection direction when compared with Doppler OCT method. The Doppler variance method is less sensitive to detection of vibration along the optical detection direction, and thus cannot detect the compression wave propagating along the OCT beam.

After obtaining the vibration information from the M scan, the propagation velocity of the shear wave at different depths of each location can be measured by calculation of the propagation depth during a time interval. The relation between the propagation velocity of the shear wave and the shear modulus is described by the simplified equation:

$$\mu_{x,z} = \rho \cdot C_{x,z}^2, \quad (2)$$

where $\mu_{x,z}$ and $C_{x,z}$ are respectively the shear modulus and the propagation velocity of the shear wave at the lateral location of x and the depth of z, and $\rho$ is the density of the soft tissue.

Young's elastic modulus, $E_{x,z}$ of a tissue-equivalent phantom is also measured directly by a MTS Synergie 100 mechanical test system. Considering the Poisson's ratio of 0.5 for the soft phantom, the relationship between shear modulus and elastic modulus is provided by the following equation:

$$E_{x,z} = 3 \cdot \mu_{x,z}. \quad (3)$$

Figure 3A:
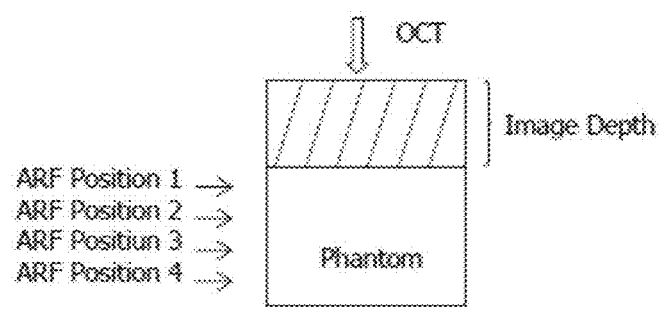
FIG. 3(a) is a schematic of the ARF excitation positions and OCT detection position. The position of OCT detection beam and the phantom are fixed. The ultrasonic transducer is moved downward at a step of 1 mm using a mechanical Z stage.
Figure 2A:
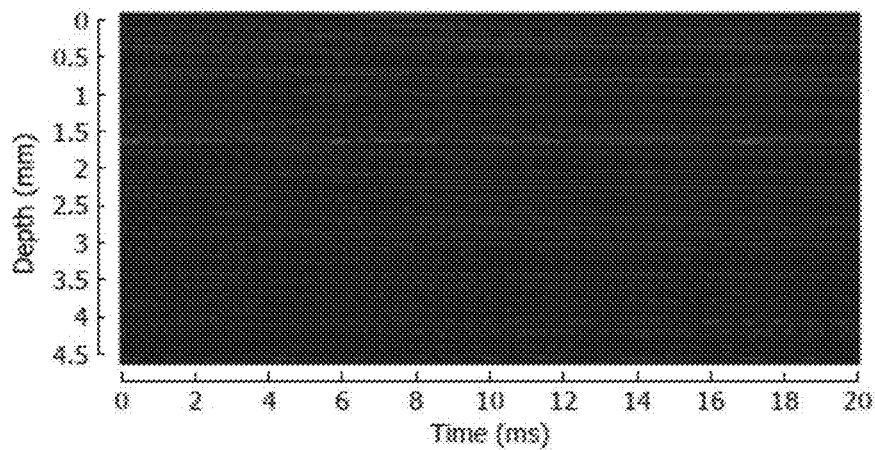
FIG. 2(a) is an M-mode OCT image of the measurement of shear wave propagation at one location as a function of depth and time. The signals are recorded during and after an ARF burst.
Figure 2B:
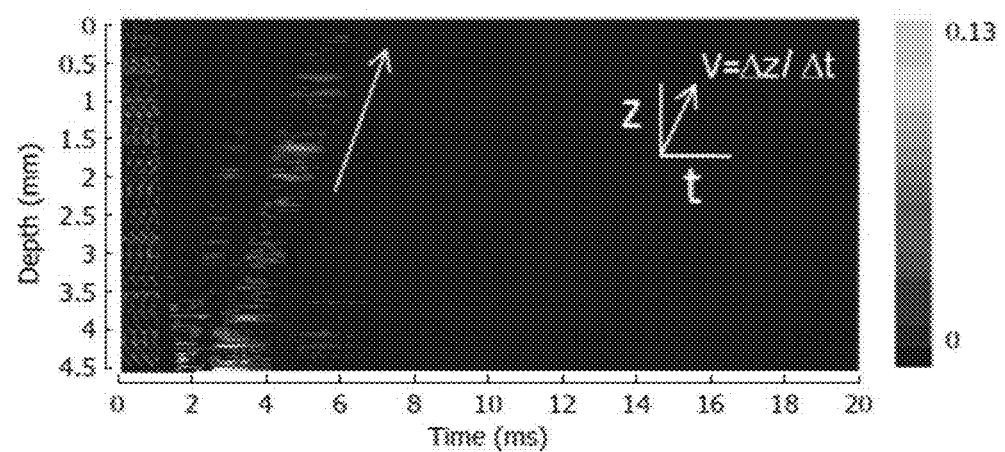
FIG. 2(b) is a Doppler variance image of the measurement of shear wave propagation at one location as a function of depth and time analyzed from the M-mode OCT data. The vibrations in a range of depths are visualized in the process of time. The arrow indicates that the shear wave propagates from the ARF focus to the surface of the phantom.
Figure 3B:
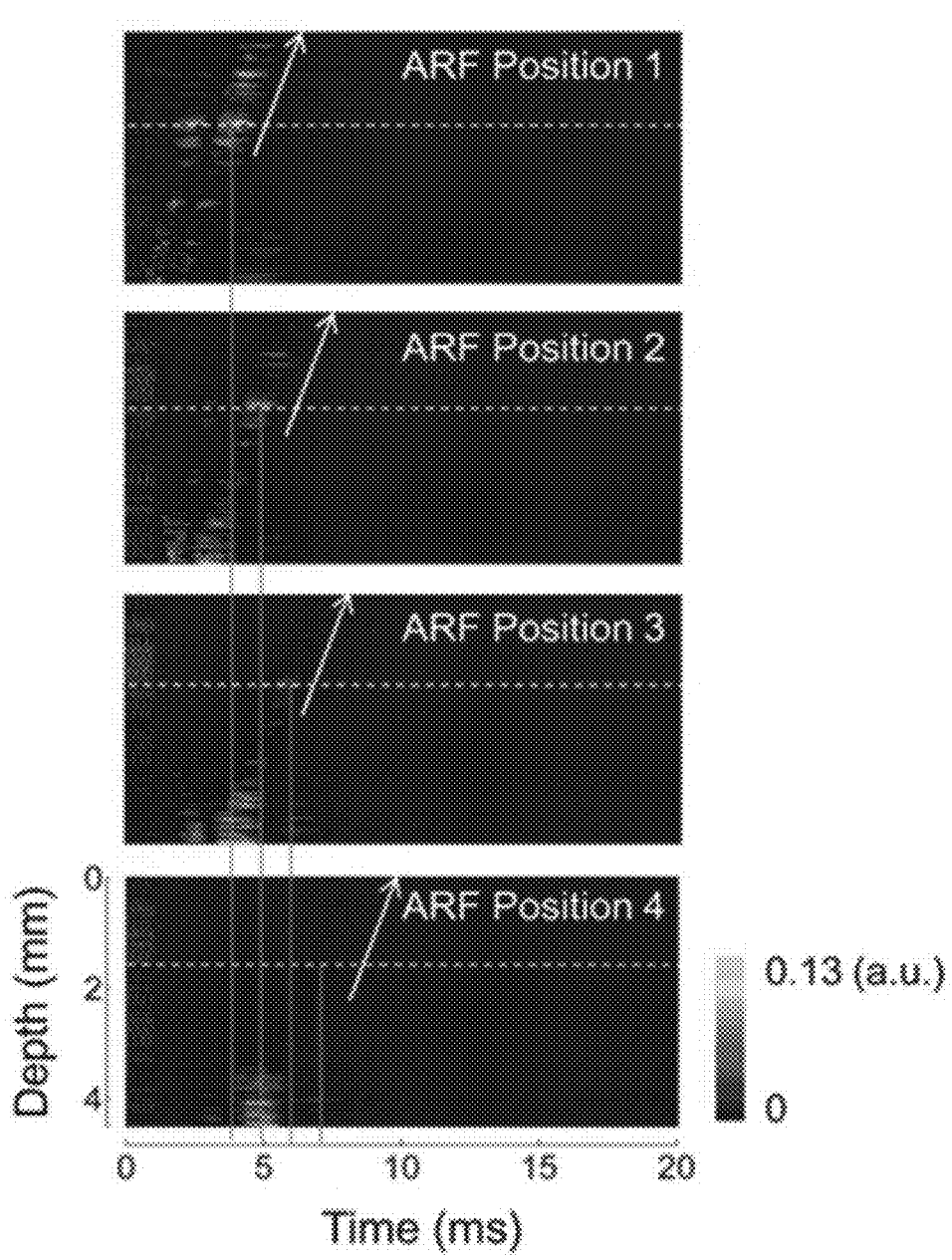
FIG. 3(b) are IBDV images with different ARF focus positions. Dashed lines indicate the same depth of the phantom and solid lines indicate the time of vibration at this depth. The vibrations at same depth are delayed when the transducer is moved downward. The propagation velocity of the shear wave around the ARF focus located at the deeper phantom can be calculated using the change of ARF position and the delay of detected vibration time.

A 0.6% agar phantom, containing 0.4% Intralipid for the increase of the backscattered signals, is detected by the ARFOE-OCT system. FIG. 2(a) shows the OCT image in M mode and FIG. 2(b) shows the corresponding IBDV image. The ultrasonic transducer generates an acoustic force, resulting in a transverse displacement of the materials in the phantom. In FIG. 2(b), high-frequency vibrations are observed during an ARF burst. After the ARF is eliminated, the induced vibrations with a lower frequency establish the shear wave propagating from the ARF focus. The shear wave propagation is parallel to the axial direction of the optical detection and perpendicular to the vibration direction. By measuring propagation depth during a time interval, the shear wave velocity can be calculated to be equal to 1.4 m/s. The corresponding shear modulus is 2.0 kPa using Eq. (2). Only an M-mode scan is required for the measurement of the shear wave propagation using this system. The data processing is much simpler than data analysis of the B scan. Due to the limit of the OCT imaging depth, the shear wave propagation can be detected in a range of the depth less than 5 mm. In order to detect the shear wave propagation in a deeper phantom, we can move the ultrasonic transducer 16 downward at a step of 1 mm [see FIG. 3(a)] using a mechanical Z stage and measure the time delay of the shear wave propagating to the same depth of the phantom. The vibrations induced by the ARF located at different positions are shown in FIG. 3(b). Right shifts of the vibrations can be observed when the transducer is moved downward because the vibrations will be delayed when the shear wave travels a longer distance. However, there are no obvious changes in propagation velocities from FIG. 3(b), so the propagation velocities in the OCT imaging area are stable. From ARF focus positions 1 to 4, the corresponding waves show intensity attenuation and time delay. The average velocity C of the shear wave propagating from position 4 to 1 can be calculated to be equal to 1.1 m/s by $\Delta D/\Delta T$, where $\Delta D$ is the distance between positions 4 and 1, and $\Delta T$ is the delay time of the detected vibration at the same depth when the ARF focus is moved from positions 1 to 4. The corresponding shear modulus calculated by Eq. (2) is 1.2 kPa. The differences of propagation velocity and shear modulus between the deeper phantom estimated by this method and the shallower phantom calculated from FIG. 2(b) may be partly due to the differences of stiffness in the phantom. The shallower layer has more moisture loss than the deeper layer in the phantom. The axial spatial resolution for shear wave measurement depends on the axial resolution of the OCT system and $\Delta Tmin \cdot C$, where $\Delta Tmin$ is the minimum A-line interval. The maximum detection depth depends on the attenuation of shear wave along the propagation direction and the sensitivity of the OCT system for the vibration detection. By moving the ARF positions to the deeper layer of a phantom, the OCE measurement depth extends to about 7.5 mm in this study, including 4.5 mm in the OCT imaging depth and about 3 mm beyond the OCT imaging depth.

Figure 4A:
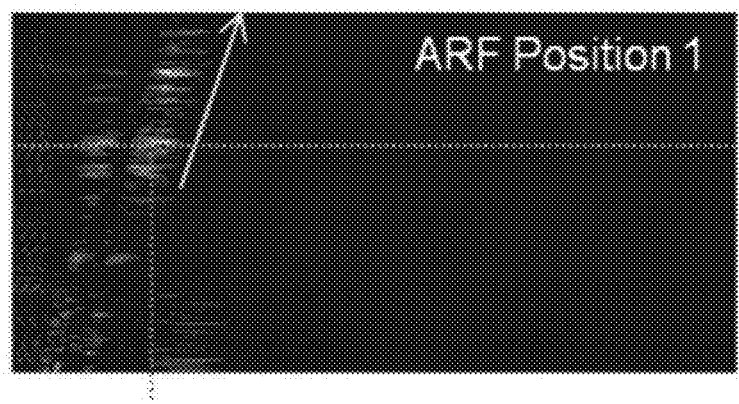
FIG. 4(a) is a cross-sectional OCT image of a bi-layer phantom. There are no obvious differences between the two layers with different agar concentrations in the phantom demarcated by a solid line.
Figure 4B:
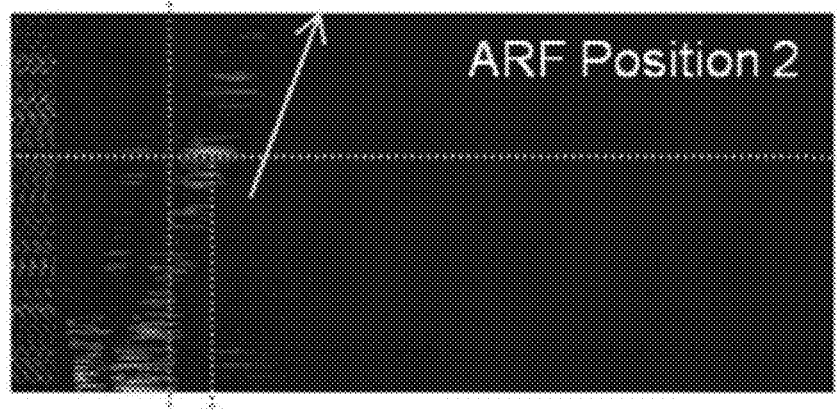
FIG. 4(b) is an IBDV image at one location of the bi-layer phantom indicated by the arrow of FIG. 4(a). The propagation velocity changes immediately when the shear wave travels through the interface of the bi-layer phantom which is indicated by a dashed line.

After detection of the shear wave in a homogeneous phantom, the cross-sectional map of the shear modulus is measured in a bi-layer phantom where the top layer is made of a 0.8% agar solution and the bottom layer is made of a 0.6% agar solution. The B-mode OCT image is shown in FIG. 4(a), and the boundary between the two layers is indicated by a white line. From the OCT image, there are no obvious differences between the two layers of the phantom with different agar concentrations. After ARF is applied and the M-mode OCT data at each location is analyzed by the IBDV method, an obvious difference of the slope between the two layers can be observed in FIG. 4(b), which shows a change in the propagation velocity through two layers. In the bottom layer of the phantom with a lower agar concentration, the stiffness is lower and the propagation velocity is lower while in the top layer of the phantom, the propagation velocity is higher due to a higher agar concentration.

Figure 4C:
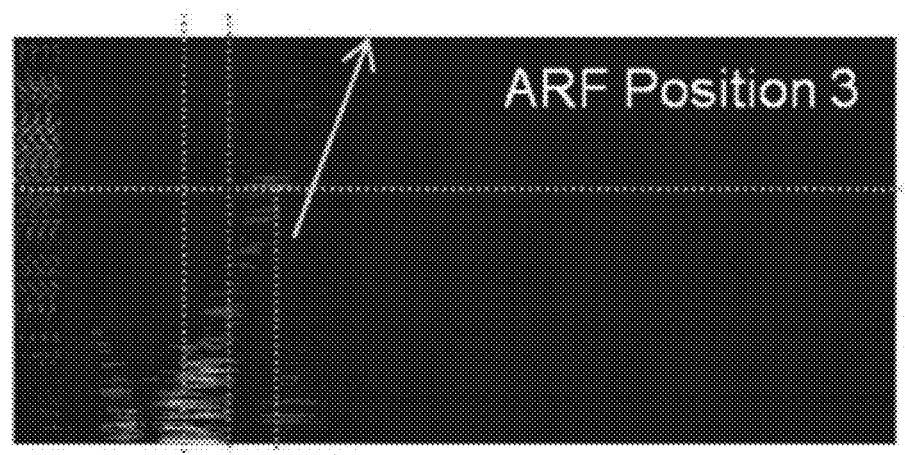
FIG. 4(c) is a cross-sectional map of the shear modulus in the bi-layer phantom. The two layers with different agar concentrations can readily be identified.

After this analysis is performed at each location incorporating B scan OCT, the distribution of the propagation velocity in a two dimensional plane can be measured. Using Eq. (2), a map of the shear modulus can be obtained, which is shown in FIG. 4(c). The boundary of two layers with different agar concentrations can be identified clearly in the phantom. The shear modulus is 9.8 kPa for the top layer and 2.2 kPa for the bottom layer, which indicates the higher stiffness in the top layer. Using a mechanical test system, the shear modulus is 5.1 kPa for a homogeneous 0.8% agar phantom and 1.2 kPa for a homogeneous 0.6% agar phantom, respectively. Here ARFOE-OCE measures the shear modulus of shallow layer in the OCT imaging range (~4 mm thickness), which may be larger than the value of a whole phantom (~10 mm thickness) measured by a mechanical test system due to more moisture loss in the shallow layer. By moving the ARF positions to the deeper layer of a phantom, the shear modulus of the deeper layer can be measured from FIG. 3, which is closer to the value from the mechanical test system.

Figure 5A:
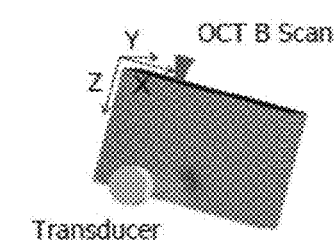
FIG. 5(a) is a schematic of the ARF excitation and OCT detection.
Figure 5B:
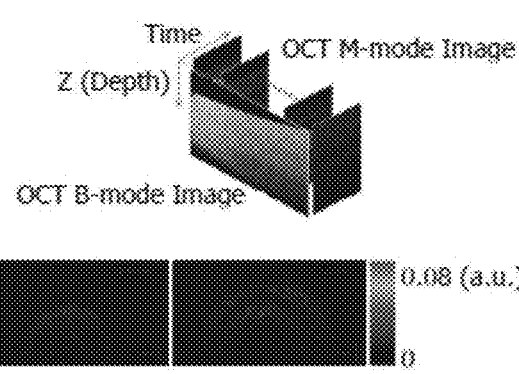
FIG. 5(b) shows OCT M-mode images and the constructed B-mode image during the measurement of shear wave.
Figure 5C:
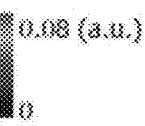
FIG. 5(c) shows Doppler variance images during the shear wave propagation in a homogeneous phantom with 0.7% agar.

FIGS. 5(a)-5(c) are color data graphs of the shear wave measurement in two dimensions. FIG. 5(a) is a schematic of the ARF excitation and OCT detection. The acoustic force is parallel to the Y axis, OCT beam is parallel to the Z axis, and the OCT B-scan is performed along the X axis. FIG. 5(b) shows OCT M-mode images and the constructed B-mode image during the measurement. The shear wave propagation in the two dimensional plane can be visualized over time, and thus, the shear wave velocity can be measured. FIG. 5(c) shows a series of Doppler variance images during the shear wave propagation in a homogeneous phantom with 0.7% agar at 0.02 ms, 0.42 ms, 0.82 ms and 1.22 ms as depicted from left to right.

Figure 6A:
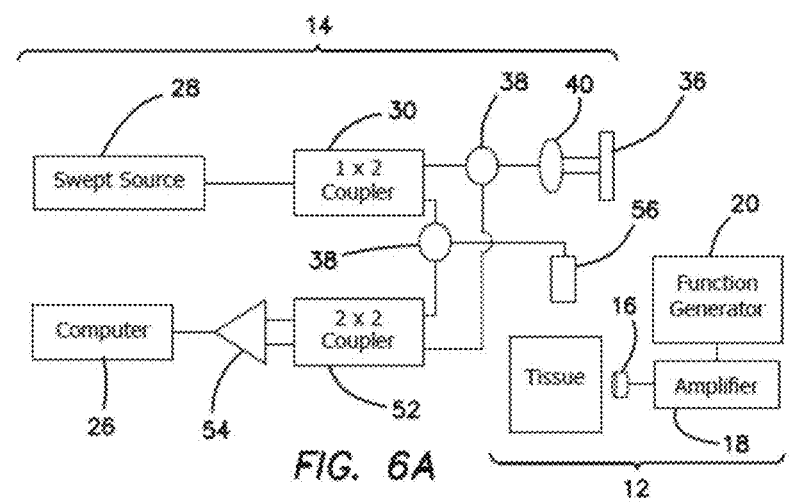
FIG. 6(a) is a schematic of an OCE system, including an OCT subsystem, an endoscope probe and an ultrasonic excitation unit.
Figure 6B:
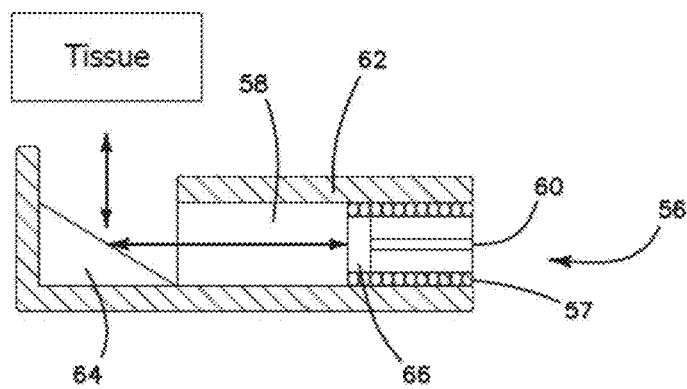
FIG. 6(b) is a schematic of the endoscope probe seen in FIG. 6(a).

FIGS. 6(a)-6(b) are diagrams of an ARF-OCE experimental setup for shear modulus measurement using an endoscope-based probe 56. FIG. 6(a) is the schematic of an OCE system 10, including an OCT subsystem 14, an ultrasonic excitation unit 12, each similar to subsystems 12 and 14 in FIG. 1 above, and an endoscope probe 56. FIG. 6(b) is the schematic of an endoscope probe 56. Rotational scanning is accomplished by using a fiber optic rotary joint (not shown) coupled with a rotational motor (not shown). Torque from the motor is translated from the proximal to the distal end of the probe by a triple wound commercial torque coil 57. Focusing of the light onto rod mirror 64 for side scanning is accomplished via a gradient index (GRIN) lens 58 together with a precisely measured spacer 66 made from no-core fiber 60. The no-core fiber 60 was first spliced and then cleaved to leave a portion at the end of a standard single mode fiber. The fiber 60 and GRIN lens 58 were attached with ultraviolet (UV) glue before placement within a custom-designed metal housing 62 for protection.

Figure 7A:
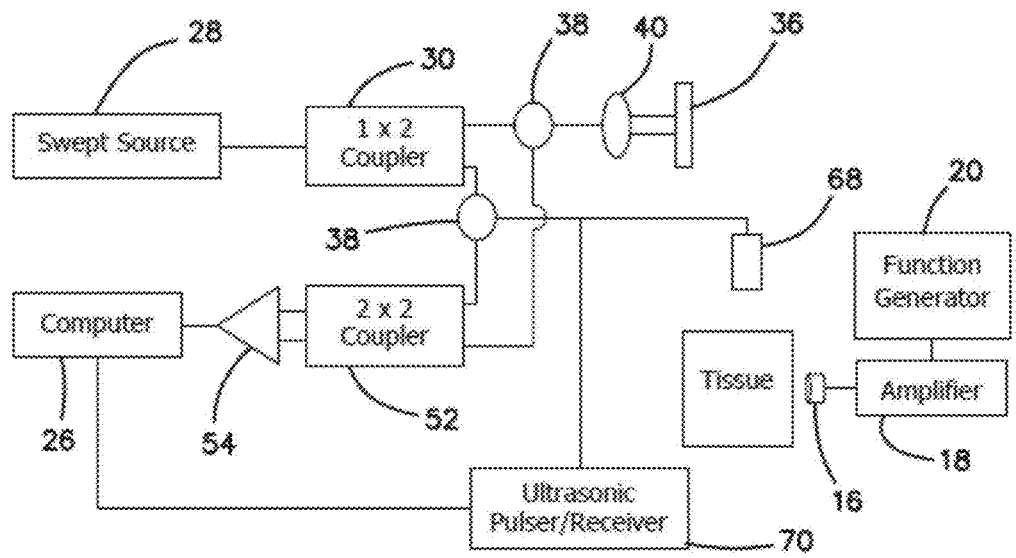
FIG. 7(a) is a schematic of an OCE system, including an OCT subsystem, an ultrasound-OCT probe, an ultrasonic pulser/receiver unit and an ultrasonic excitation unit.
Figure 7B:
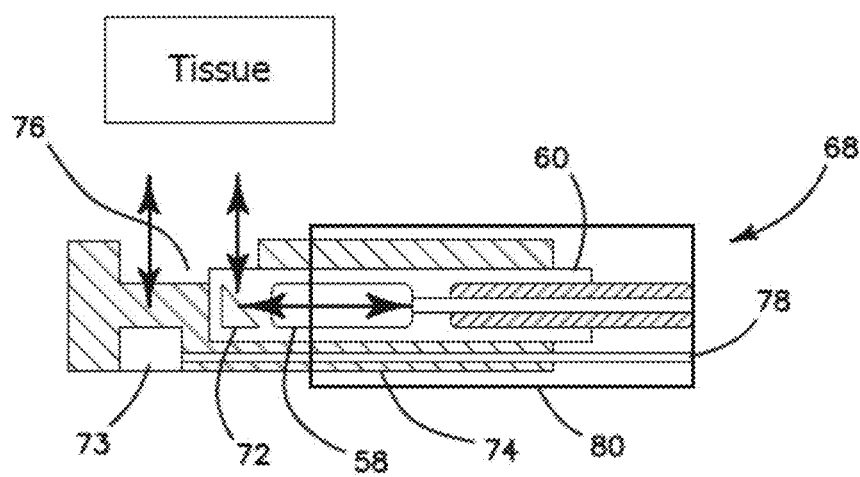
FIG. 7(b) is a schematic of the integrated ultrasound-OCT probe seen in FIG. 7(a).

FIGS. 7(a)-7(b) are diagrams of an ARF-OCE experimental setup for shear modulus measurement using an integrated ultrasound-OCT probe 68. FIG. 7(a) is the schematic of an OCE system 10, including an OCT subsystem 14, an ultrasound-OCT probe 68, an ultrasonic pulser/receiver unit 70 and an ultrasonic excitation unit 12. The pulser/receiver unit 70 is used to drive the ultrasound transducer 16 and also to receive the echo signals.

FIG. 7(b) is the schematic of an integrated ultrasound-OCT probe. Within the probe 68, a gradient index (GRIN) lens 58 is used for light focusing, followed by a micro-prism 72 for reflecting the focused light beam into tissue. All the optical components were fixed in a polyimide tube 74. The ultrasonic transducer 73 was built using a PMN-PT single crystal which has superior piezoelectric properties for building high sensitivity US transducers in a small size. The transducer 73 is fixed in the proximal end of a thin-wall polyimide tube 74 within which the OCT probe 54 is also fixed. A window 76 is defined in the tube 74 to let both the light beam and soundwave exit. Finally, the transducer wire 78 and optical fiber 60 are sealed in a thin-wall fluorinate ethylene propylene (FEP) tube 80. The OCT-US probe 68 is connected to the integrated OCT-US system 10 via a rotary joint (not shown) which is comprised of a fiber optic rotary joint (not shown) and an electric slip ring (not shown).

Figure 8A:
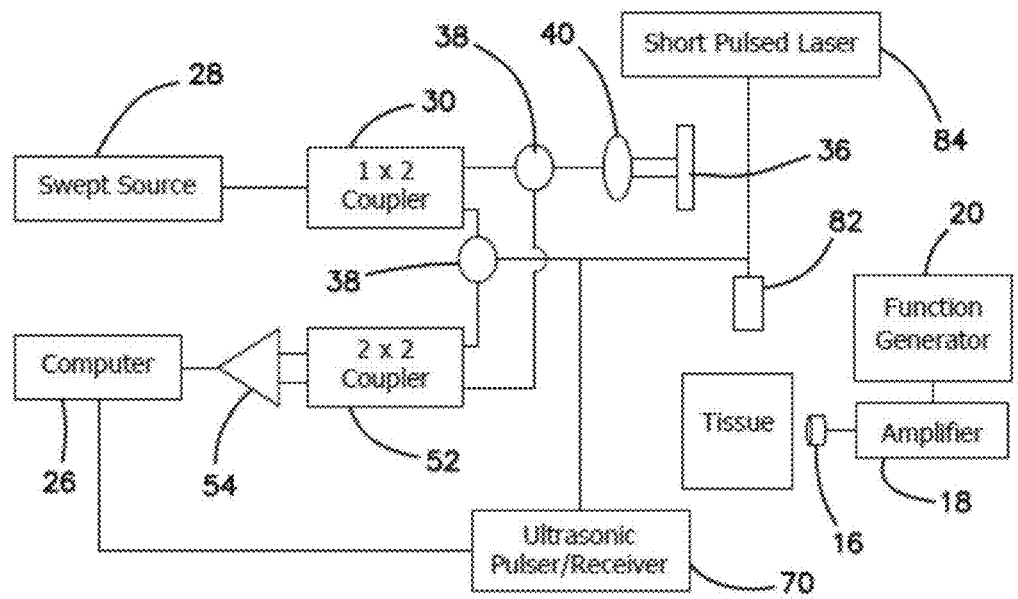
FIG. 8(a) is a schematic of an OCE system, including an OCT subsystem, a photoacoustic-OCT probe, an ultrasonic pulser/receiver unit, a short pulsed laser for generation of ultrasound signal and an ultrasonic excitation unit.
Figure 8B:
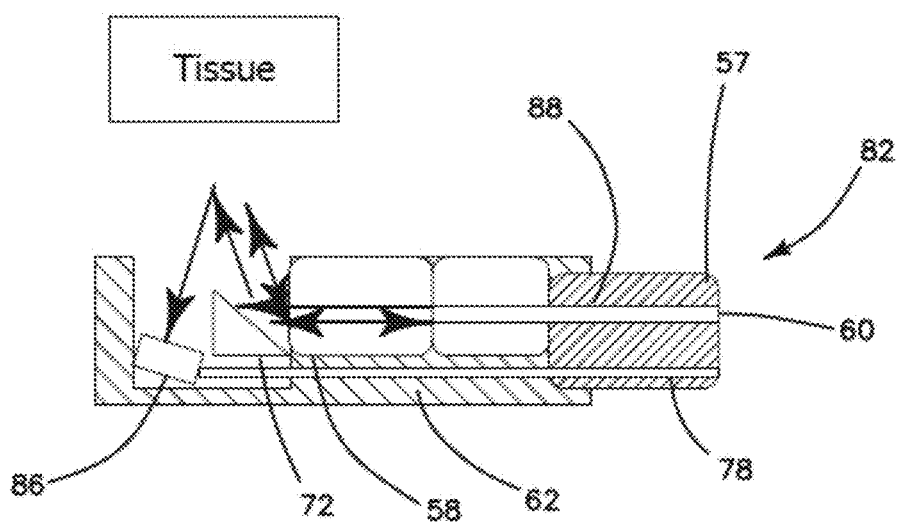
FIG. 8(b) is a schematic of the integrated photoacoustic-OCT probe seen in FIG. 8(a).

FIGS. 8(*a*)-8(*b*) are diagrams of an ARF-OCE experimental setup for shear modulus measurement using an integrated photoacoustic-OCT probe 82. FIG. 8(*a*) is the schematic of an OCE system 10, including an OCT subsystem 14, a photoacoustic-OCT probe 68, an ultrasonic pulser/receiver unit 70, a short pulsed laser 84 for generation of ultrasound signal and an ultrasonic excitation unit 12. The pulser/receiver unit 70 is used to receive the echo signals.

FIG. 8(*b*) is the schematic of an integrated photoacoustic-OCT probe 82. Torque from the motor (not shown) is translated from the proximal to the distal end of the probe 82 by a triple wound commercial torque coil 57. The light from a short pulsed laser 84 and a swept source 28 arrive at a GRIN lens 58 through double-cladding fiber 60. After focusing by a GRIN lens 58, the light from laser 84 and from swept source 28 are reflected to the tissue by a prism 72. Ultrasound signals generated by the absorption of short pulsed laser 84 inside the tissue are received by an ultrasound transducer 86. The fiber 60 and GRIN lens 58 were attached with ultraviolet (UV) glue and a ferrule 88 before placement within a metal housing.

Figure 9A:
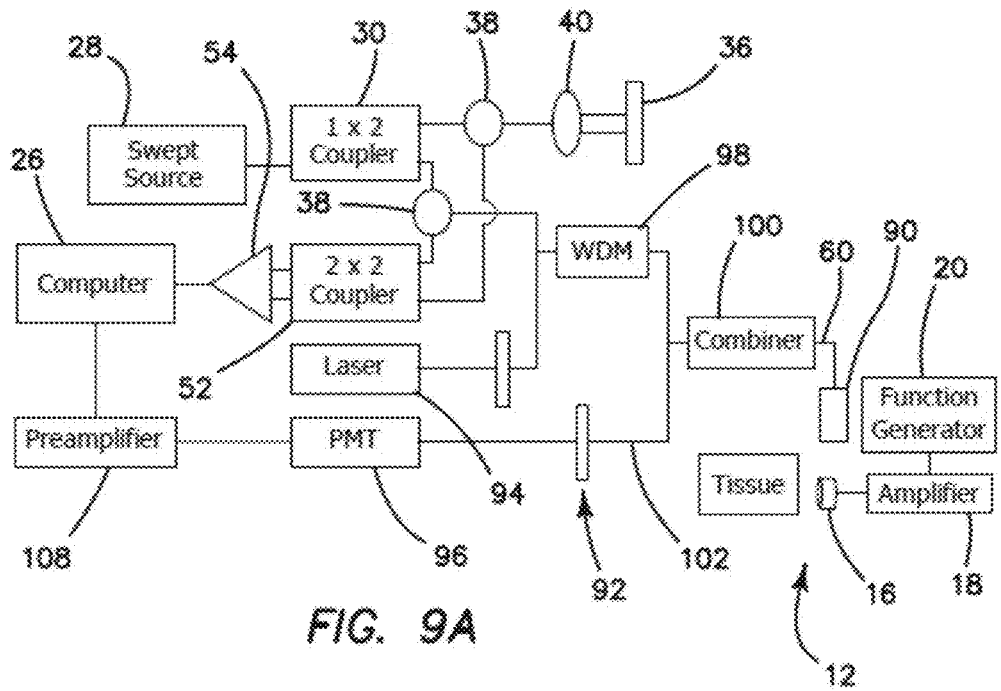
FIG. 9(a) is a schematic of an OCE system, including an OCT subsystem, a fluorescence-OCT probe, a fluorescence excitation/detection unit and an ultrasonic excitation unit.
Figure 9B:
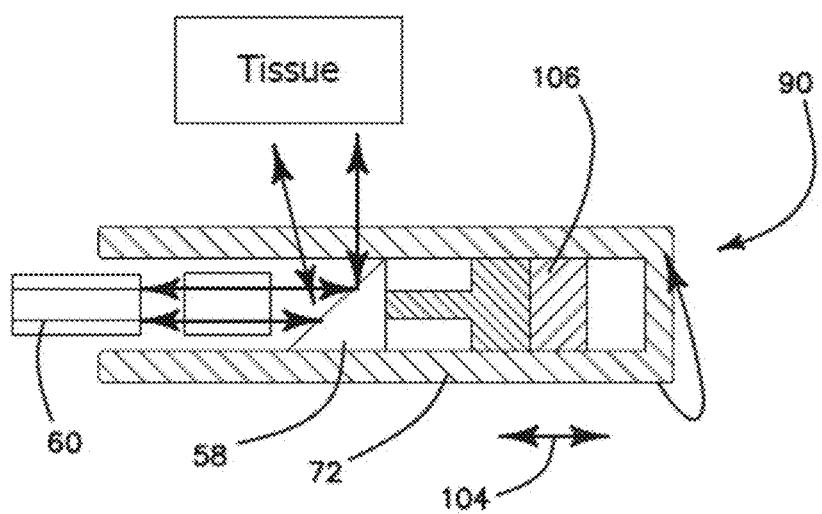
FIG. 9(b) is a schematic of the integrated fluorescence-OCT probe seen in FIG. 9(a).

FIGS. 9(*a*)-9(*b*) are diagrams of an ARF-OCE experimental setup for shear modulus measurement using an integrated fluorescence-OCT probe 90. FIG. 9(*a*) is the schematic of an OCE system 10, including an OCT subsystem 14, a fluorescence-OCT probe 90, a fluorescence excitation/detection unit 92 and an ultrasonic excitation unit 12. A continuous-wave laser diode 94 is used as the fluorescence excitation source. A photomultiplier tube (PMT) 96 is used to detect fluorescence emission light. The excitation light and the OCT beam are combined together with a wavelength division multiplexer 98. A double-clad fiber (DCF) combiner 100 with one single-mode fiber port, one multimode fiber port, and one DCF port is used to deliver the OCT and fluorescence excitation light beams to the tissue sample and collect the OCT signal and fluorescence emission light. The OCT signal and fluorescence excitation light are transported through the core of the DCF 102, and the back-reflected fluorescence emission light is collected through the inner cladding of the DCF 102. Fluorescence emission light back-scattered from the tissue sample is coupled back through the multimode fiber port of the combiner 100 and detected by the PMT 96 to be preamplified by preamplifier 108 and coupled to computer 26.

FIG. 9(*b*) is the schematic of an integrated fluorescence-OCT probe 90. A linear motor (not shown) outside the endoscope is used to pull back the entire probe 90 as indicated symbolically by arrow 104 to create a three dimensional helical OCT scan and achieve a two dimensional superficial fluorescence intensity image. The OCT beam and fluorescence excitation light is transmitted through fiber 60 from combiner 100 through GRIN lens 58 to a rotatable prism 72, which is rotated by in-probe micromotor 106. Fluorescence emission and OCT light back-scattered from the tissue sample returns by the same optical path in probe 90.

Figure 10A:
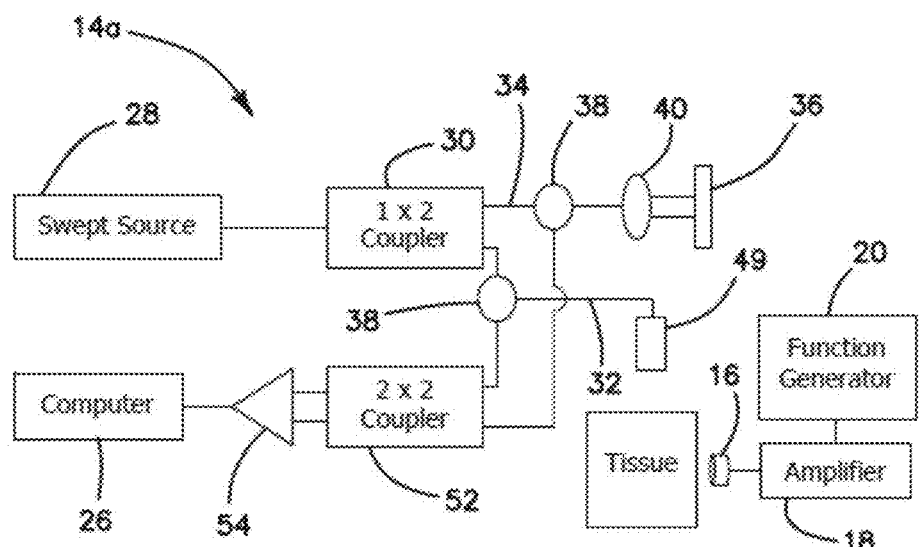
FIG. 10(a) is an ARF-OCE diagram based on a swept-source OCT system.
Figure 10B:
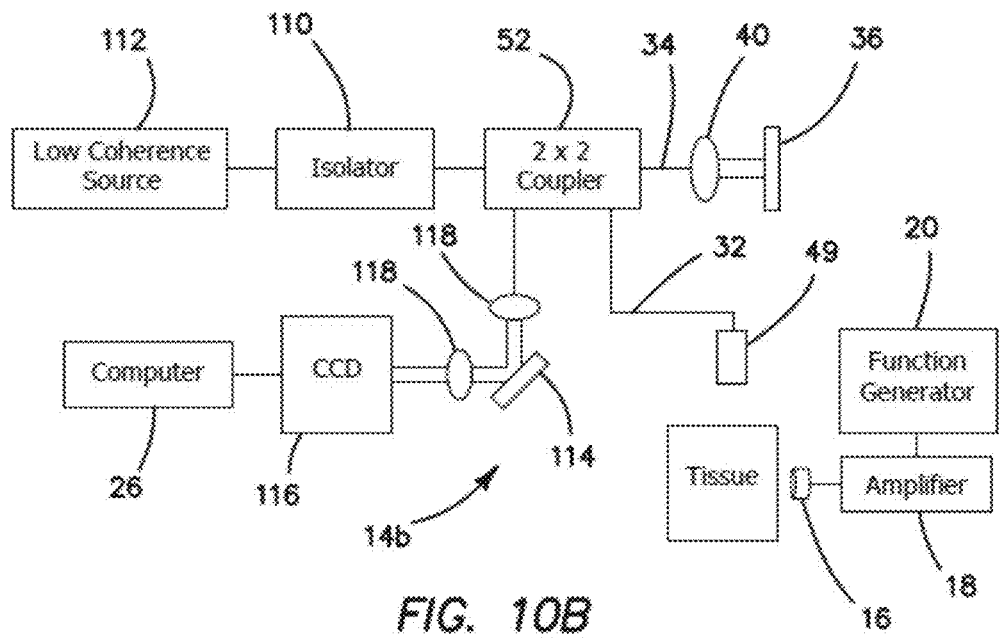
FIG. 10(b) is an ARF-OCE diagram based on a Fourier-domain OCT system.

FIGS. 10(*a*) and 10(*b*) are diagrams of ARF-OCE experimental setup based on two different OCT systems 14. FIG. 10(*a*) is an ARF-OCE diagram based on a swept-source OCT system 14*a* as shown in FIG. 1. The light from the swept source 28 is split into the sample arm 32 and the reference arm 34. In the sample arm 32, the light reaches the tissue through a circulator 38 and a scan lens (or a probe) 49. In the reference arm 34, the light is reflected by a mirror 36 after passing through a circulator 38 and a collimator 40. The light from the sample arm 32 and from the reference arm 34 interfere in a coupler 52 and is detected by a detector 54.

FIG. 10(*b*) is an ARF-OCE diagram based on a Fourier-domain OCT system 14*b*. After passing through an isolator 110, the light from a low coherence source 112 is split into the sample arm 32 and the reference arm 34. In the reference arm 34, the light is reflected by a mirror 36. In the sample arm 32, the light reaches the tissue through a scan lens or a probe 49. The light from the sample arm 32 and from the reference arm 34 interfere in a coupler 52. The interference light is focused by optics 118 and split and diffracted by a diffraction grating 114 into several beams in different directions and is detected by a CCD camera 116.

Figure 11A:
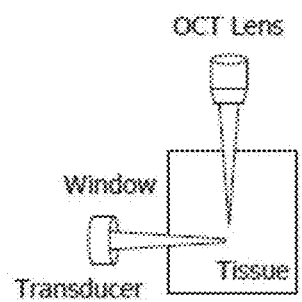
FIG. 11(a) shows the ARF-OCE system in which the ARF is perpendicular to the OCT beam.
Figure 11B:
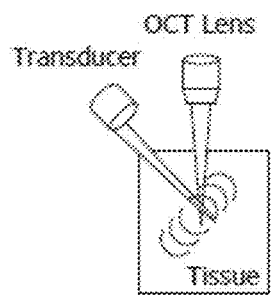
FIG. 11(b) shows the ARF-OCE system in which the ARF has a perpendicular component to the OCT beam.
Figure 11C:
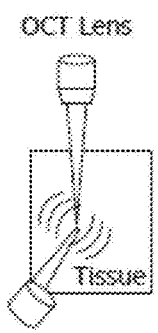
FIG. 11(c) shows an alternative embodiment of the ARF-OCE system in which the ARF has a different perpendicular component to the OCT beam from the embodiment seen in FIG. 11(b).

FIGS. 11(*a*)-11(*c*) show the ARF excitation direction in the OCE experimental setup. FIG. 11(*a*) shows the ARF-OCE system 10, in which the ARF is perpendicular to the OCT beam. FIG. 11(*b*) and FIG. 11(*c*) show the ARF-OCE system 10, in which the ARF has a perpendicular component to the OCT beam.

ARF-OCE has the ability to noninvasively map biomechanical properties inside a soft tissue benefitting from the high resolution of OCT and noncontact force generation. ARFOE-OCE system using orthogonal ARF excitation and Doppler variance measurement has four advantages compared with previous methods. First, our configuration can provide higher axial resolution and greater depth for shear wave measurement, compared with previous co-aligned setups. The OCE measurement depth extends beyond the OCT imaging depth.

Second, the shear modulus at one location can be measured using the M mode without the need of a B scan. The data processing method will be simpler and quicker, and the system will be simplified when the elastic parameter of a fixed location is required.

Third, this system uses Doppler variance to measure shear wave, which is more stable than the previous OCE systems based on the phase shift measurement and will not be distorted by bulk motion and phase wrapping.

Finally, co-aligned ARF excitation requires a ring transducer, which is difficult to implement. In current ARF-OCE setups for the ophthalmic applications, ARF excites the sample with an oblique angle to the imaging plane so that it does not block the OCT imaging beam. The ARF-induced vibration may not be parallel to the OCT beam, which will result in the low sensitivity for phase detection and complicated wave propagation for the analysis. In addition, co-aligned ARF excitation requires the use of an ultrasound gel between the transducer and the central cornea, which may change the biomechanical properties of ocular tissues.

Orthogonal ARF excitation system provides a new opportunity for the probe design in the ophthalmic applications. The ultrasonic wave could reach the target tissue through the outer corner of the eye or the eyelid without affecting the cornea. The ARFOE-OCE system incorporating orthogonal ARF excitation and Doppler variance method has great potential for in vivo clinical applications where high axial resolution, great depth, and noninvasive mapping of the shear modulus is important.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for imaging a shear wave or quantifying shear modulus in tissue under orthogonal acoustic radiation force (ARF) excitation using an optical coherence tomography (OCT) Doppler variance acquisition system comprising:
   generating an OCT beam in the tissue;
   generating ARF-induced vibration in the tissue which is at least partially perpendicular relative to the OCT beam in the tissue by an ultrasonic transducer;
   detecting ARF-induced vibration in the tissue with an OCT probe or lens;
   imaging a shear wave propagation with the OCT probe or lens; and
   mapping the shear modulus from the imaging of the shear wave propagation.

2. The method of claim 1 where imaging a shear wave propagation with the OCT probe or lens comprises imaging a shear wave propagation with at least a parallel component to the OCT beam by performing an M-mode scan at a plurality of locations and quantitatively measuring a slope of a propagation path to calculate shear modulus at each of the plurality of locations.

3. The method of claim 1 where mapping the shear modulus from the imaging of the shear wave propagation further comprises quantitatively mapping the shear modulus of a volume in the tissue by performing a lateral and transverse scan relative to the tissue to map the shear modulus of the tissue.

4. The method of claim 1 where detecting ARF-induced vibration in the tissue with the OCT probe or lens comprises using an intensity based Doppler variance (IBDV) quantitative measurement.

5. The method of claim 2 where mapping the shear modulus from the imaging of the shear wave propagation further comprises quantitatively mapping the shear modulus of a cross-section in the tissue by performing a cross-sectional B scan.

6. The method of claim 1 further comprising quantitatively mapping Young's modulus, a velocity of the shear wave or a combination thereof of a volume in the tissue by performing a lateral and transverse scan relative to the tissue.

7. The method of claim 1 where generating ARF-induced vibration in the tissue which is at least partially perpendicular relative to the OCT beam in the tissue by an ultrasonic transducer comprises generating the ARF-induced vibration by a remote ultrasonic transducer applying a non-contact force to the tissue.

8. The method of claim 1 where generating ARF-induced vibration in the tissue which is at least partially perpendicular relative to the OCT beam in the tissue by an ultrasonic transducer comprises generating the ARF-induced vibration by an ultrasonic transducer applying a contact force to the tissue.

9. The method of claim 1 where generating ARF-induced vibration in the tissue which is at least partially perpendicular relative to the OCT beam in the tissue by an ultrasonic transducer comprises generating an ARF-induced vibration which is entirely perpendicular to the OCT beam.

10. The method of claim 1 where generating an OCT beam and detecting ARF-induced vibration in the tissue with the OCT probe or lens comprises using an endoscope-based system.

11. The method of claim 1 where generating the OCT beam in the tissue and detecting ARF-induced vibration in the tissue with the OCT probe or lens comprises generating an OCT beam in the tissue and detecting ARF-induced vibration in the tissue with a multimodality system comprising an integrated ultrasound-OCT system, an integrated photoacoustic-OCT system, or an integrated fluorescence-OCT system.

12. The method of claim 1 where generating the OCT beam in the tissue and detecting ARF-induced vibration in the tissue with the OCT probe or lens comprises generating the OCT beam in the tissue and detecting ARF-induced vibration in cancer tissue, ocular tissue, periocular tissue or vascular tissue with the OCT probe or lens.

13. An apparatus for imaging a shear wave or quantifying shear modulus in tissue under orthogonal acoustic radiation force (ARF) excitation using an optical coherence tomography (OCT) Doppler variance acquisition system comprising:
- an OCT subsystem for generating an OCT beam in the tissue;
- an ARF subsystem for generating an ARF-induced vibration in the tissue which is at least partially perpendicular relative to the OCT beam in the tissue by an ultrasonic transducer; and
- a detector coupled to the OCT subsystem for detecting ARF-induced vibration in the tissue,
- where the OCT subsystem comprises an OCT probe or lens.

14. The apparatus of claim 13 where the ARF subsystem comprises a remote ultrasonic transducer applying a non-contact force to the tissue.

15. The apparatus of claim 13 where the ARF subsystem comprises an ultrasonic transducer applying a contact force to the tissue.

16. The apparatus of claim 13 where the OCT probe or lens comprises an endoscope-based system.

17. The apparatus of claim 13 further comprising an integrated ultrasound-OCT system, an integrated photoacoustic-OCT system, or an integrated fluorescence-OCT system.

* * * * *